(12) United States Patent
Kaushal et al.

(10) Patent No.: US 8,150,506 B2
(45) Date of Patent: Apr. 3, 2012

(54) METHODS AND DEVICES FOR DIFFERENTIATING BETWEEN TISSUE TYPES

(75) Inventors: Shalesh Kaushal, Worcester, MA (US); Michael Darnall Furman, Cambridge (GB); Jennifer Delight Simonotto, Newcastle upon Tyne (GB); Abraham Miliotis, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 12/440,767

(22) PCT Filed: Sep. 12, 2007

(86) PCT No.: PCT/US2007/078290
§ 371 (c)(1),
(2), (4) Date: Sep. 10, 2009

(87) PCT Pub. No.: WO2008/033937
PCT Pub. Date: Mar. 20, 2008

(65) Prior Publication Data
US 2010/0063498 A1 Mar. 11, 2010

Related U.S. Application Data

(60) Provisional application No. 60/843,992, filed on Sep. 12, 2006.

(51) Int. Cl.
*A61B 5/04* (2006.01)
*A61B 5/05* (2006.01)
*A61B 10/00* (2006.01)
*A61B 17/24* (2006.01)

(52) U.S. Cl. ........ 600/547; 600/383; 600/564; 600/569; 600/570; 606/161

(58) Field of Classification Search .......... 600/383, 600/547, 564, 569, 570; 606/161
See application file for complete search history.

(56) References Cited

U.S. PATENT DOCUMENTS

| | | | | | |
|---|---|---|---|---|---|
| 4,174,715 | A | * | 11/1979 | Hasson | 606/206 |
| 4,417,581 | A | * | 11/1983 | Dawson | 600/383 |
| 4,483,133 | A | * | 11/1984 | Pasley | 56/400.06 |
| 4,874,237 | A | * | 10/1989 | Cringle | 221/221 |
| 5,053,041 | A | * | 10/1991 | Ansari et al. | 606/148 |
| 5,154,174 | A | | 10/1992 | Hawlina | |
| 5,578,040 | A | * | 11/1996 | Smith | 606/41 |
| 5,833,619 | A | * | 11/1998 | Freed et al. | 600/485 |
| 6,176,856 | B1 | | 1/2001 | Jandak et al. | |
| 6,453,906 | B1 | * | 9/2002 | Taylor et al. | 128/898 |
| 6,678,552 | B2 | | 1/2004 | Pearlman | |

(Continued)

FOREIGN PATENT DOCUMENTS

GB 2 423 255 8/2006

(Continued)

*Primary Examiner* — Max Hindenburg
*Assistant Examiner* — Sean Dougherty
(74) *Attorney, Agent, or Firm* — Saliwanchik, Lloyd & Eisenschenk

(57) ABSTRACT

The subject invention utilizes the characteristics of in vivo tissue impedances to provide an embodiment of a retinal rake capable of providing a visible and/or preferably an audible signal to a surgeon that more clearly indicates which type of tissue(s) is in contact with the retinal rake. A preferred embodiment comprises a handheld, battery operated retinal rake having two electrodes, wherein at least one electrode is the modified retinal rake. Upon contact with different optical tissues, e.g., epiretinal membranes, retinal tissue, vitreous humor, etc., the electrodes detect varying impedances which are translated by onboard circuitry into various signals that indicate what type of tissue, fluid, structure, etc. is in contact with the retinal rake.

8 Claims, 7 Drawing Sheets

U.S. PATENT DOCUMENTS

| | | |
|---|---|---|
| 2002/0087155 A1* | 7/2002 | Underwood et al. ............ 606/32 |
| 2002/0128641 A1* | 9/2002 | Underwood et al. ............ 606/32 |
| 2003/0120305 A1* | 6/2003 | Jud et al. ...................... 606/205 |
| 2005/0215945 A1* | 9/2005 | Harris et al. ..................... 604/66 |
| 2006/0030833 A1* | 2/2006 | Harris et al. ................... 604/503 |
| 2006/0116703 A1 | 6/2006 | Glaser |
| 2006/0129145 A1* | 6/2006 | Woloszko et al. .............. 606/41 |

FOREIGN PATENT DOCUMENTS

| | | |
|---|---|---|
| WO | WO 02/32335 | 4/2002 |
| WO | WO 2004/075928 | 9/2004 |

\* cited by examiner

METHODS AND DEVICES FOR DIFFERENTIATING BETWEEN TISSUE TYPES

CROSS-REFERENCE TO A RELATED APPLICATION

This application is a National Stage Application of International Application Number PCT/US2007/078290, filed Sep. 12, 2007; which claims the benefit of U.S. Provisional Application No. 60/843,992, filed Sep. 12, 2006, both of which are incorporated herein by reference in their entirety.

BACKGROUND OF INVENTION

Vitreoretinal surgery is an invasive microsurgical ocular procedure utilized to correct problems at or near the back of the eye. It is particularly useful for correcting retinal disorders, such as removal of various types of potentially vision-impairing or destructive epiretinal membranes (ERMs). In this type of ophthalmic surgery (pars plana vitrectomy), surgeons access the back of the eye through standard procedures and utilize various instruments, for example, a "retinal rake", to remove these membrane(s) by scraping or scouring the surface of the retina.

When conducting vitreoretinal surgeries it is important to remove, manipulate and/or contact only diseased or scarred tissue to minimize damage to healthy surrounding or underlying tissues. As expected, this is especially important when addressing problems of, or near, the retina.

Prior to such surgeries, a pre-surgical image is often obtained, such as a fluoroscein image, of the pertinent ocular structure, such as the eye retina. This can provide a surgeon with information about the type and/or extent (e.g., depth, area, etc.) of the membrane or other tissue to be removed. During surgery, a slit lamp is usually utilized to view the interior of the eye while a surgeon manually removes the epiretinal membranes. The surgeon must often rely on experience and visual observation, through the slit lamp or other visual device, to determine where and how much material to remove. There is little, if any, other feedback to a surgeon during the procedure as to what type of tissues are being touched or manipulated.

This difficulty in differentiating between tissue types creates challenges in other types of surgeries including, for example, surgeries to remove tissue adjacent to nervous system tissue.

Therefore, a need exists for a surgical instrument capable of providing a secondary signal to surgeons to distinguish between touching healthy eye tissue and tissue that needs to be removed. In particular, there exists a need for a retinal rake or similar device that can identify epiretinal membranes (ERMs) and retinal tissue and provide a signal to indicate which tissue is in contact with the retinal rake.

BRIEF SUMMARY

Various in vivo healthy and diseased tissues or fluids within a body have different, detectable electrical conductivities. For example, fat tissue cells have a relatively high impedance because of their low water content (10-20%), whereas more fat-free tissues tend to have relatively lower impedances because of their higher water content (70-75%). In a specific example, epiretinal membranes (ERMs) have a relatively high electrical impedance, which causes them to be relatively electrically inactive. However, retinal tissue has a lower electrical impedance, which causes it to be relatively electrically active. It is this difference in impedance in various tissues that is detectable according to the subject invention and can be isolated and distinguished to differentiate tissues.

Specifically, the subject invention utilizes these characteristics of in vivo tissue impedances to provide a retinal rake, or similar device or instrument, capable of providing a more visible signal and/or an audible signal to a surgeon that clearly identifies which type of tissue(s) is in contact with the retinal rake.

In one embodiment, the signal is visual, where one or more lights are utilized and/or a change in light intensity indicates the type of tissue and/or how much contact is made with the device or instrument. In another embodiment, the signal is auditory where a tone or sound change can indicate contact with active, inactive or inert tissues.

BRIEF DESCRIPTION OF DRAWINGS

In order that a more precise understanding of the invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which.

DETAILED DISCLOSURE

The subject invention provides embodiments of medical instruments and/or devices capable of identifying which type of in vivo tissue is in contact with the instrument or device and providing one or more visible and/or an audible signals to the use of the device. More specifically, the subject invention pertains to a retinal rake, or similar device, capable of providing one or more visible signals and/or audible signals to a surgeon to more clearly identify which type of in vivo tissue(s) is in contact with the device. The subject invention also provides methods of uses for the instruments described herein.

The subject invention is particularly useful in the field of optical surgical procedures, and in particular for devices used for the treatment and/or removal of epiretinal membranes (ERMs). However, a person with skill in the art will be able to recognize other uses that would be applicable to the devices and methods of the subject invention. While the subject application describes a use for treatment and/or removal of ERMs, other modifications apparent to a person with skill in the art and having benefit of the subject disclosure are contemplated to be within the scope of the present invention.

The term "patient" as used herein, describes an animal, including mammals to which the systems and methods of the present invention are provided. Mammalian species that can benefit from the disclosed systems and methods include, but are not limited to, apes, chimpanzees, orangutans, humans, monkeys; domesticated animals (e.g., pets) such as dogs, cats, guinea pigs, and hamsters, cattle, horses, goats, sheep, or any wild animal for veterinary or tracking purposes.

The term "physician", as used herein, describes any individual trained in the medical arts capable of using the devices or methods of the subject invention. Such individuals can include, but are not limited to, general practice physicians, specializing surgeons, nurses, physician assistants, interns, other trained support staff, etc.

Also, as used herein, and unless otherwise specifically stated, the terms "operable communication" and "operably connected" mean that the particular elements are connected in such a way that they cooperate to achieve their intended function or functions. The "connection" may be direct, or indirect, physical or remote.

In addition, references to "first", "second", and the like (e.g., first and second electrode), as used herein, and unless otherwise specifically stated, are intended to identify a particular feature of which there are at least two. However, these references are not intended to confer any order in time, structural orientation, or sidedness (e.g., left or right) with respect to a particular feature.

Figure 1:
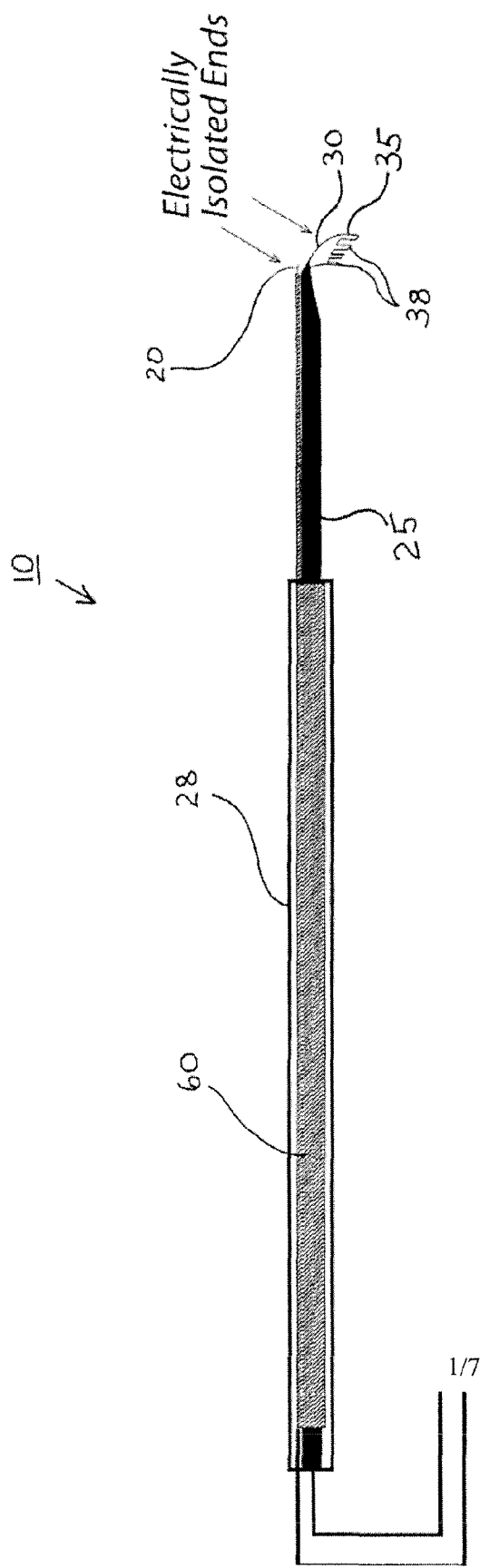
FIG. 1 is an illustration of one embodiment of the device of the subject invention.
Figure 3A:
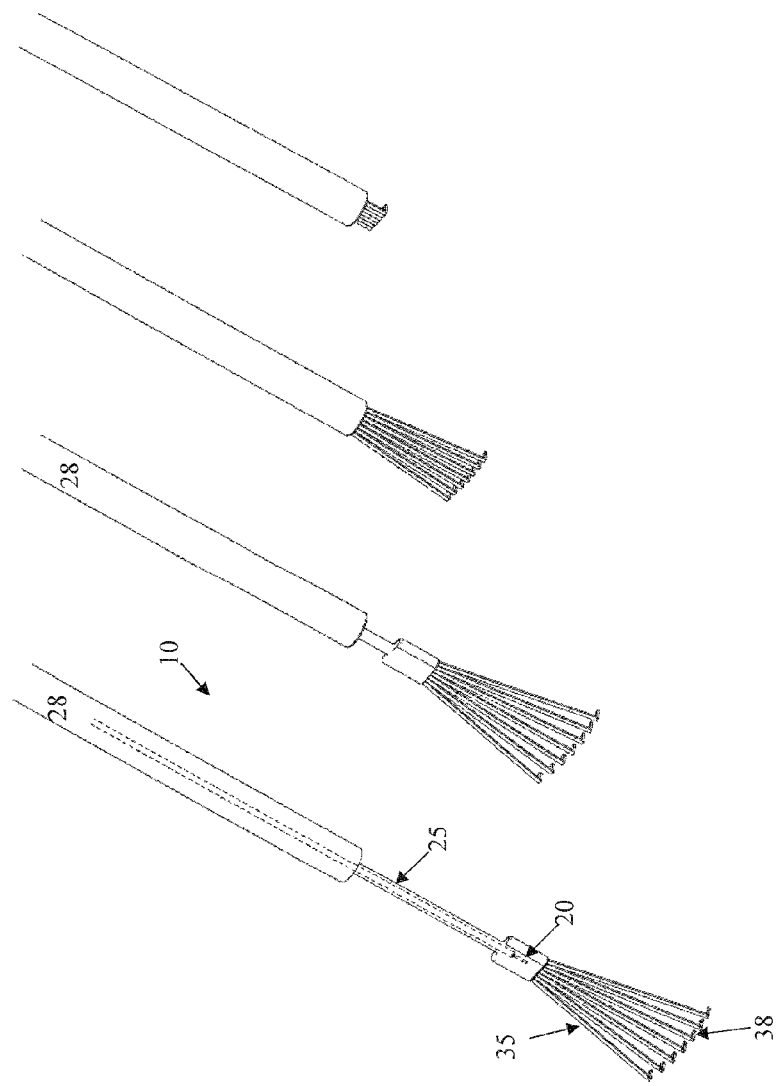
FIG. 3A illustrates a typical retinal rake device that can be modified according to the subject invention.

With reference to the attached figures, which show certain embodiments of the subject invention, it can be seen in FIG. 1 that an embodiment of the subject invention comprises a retinal rake modified to detect electrical impulses. As mentioned above, there are several devices including retinal rakes that can be modified according to the embodiments of the subject invention. For example, in one embodiment, a Glaser Flexible Rake as shown in FIG. 3A can be utilized according to the teachings of the subject invention.

Figure 3B:
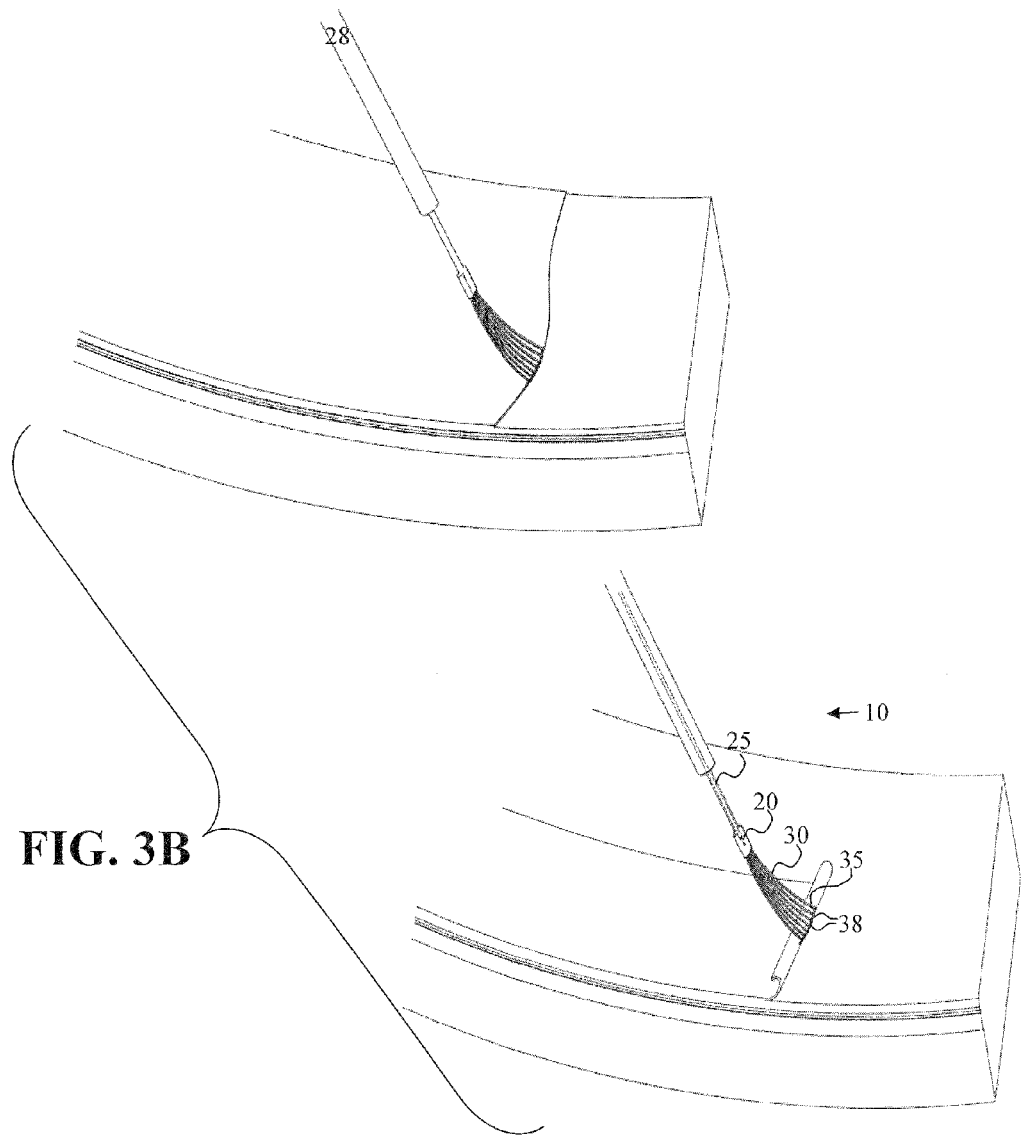
FIG. 3B illustrates a typical retinal rake device being used to treat or remove in vivo epiretinal membranes.
Figure 4A:
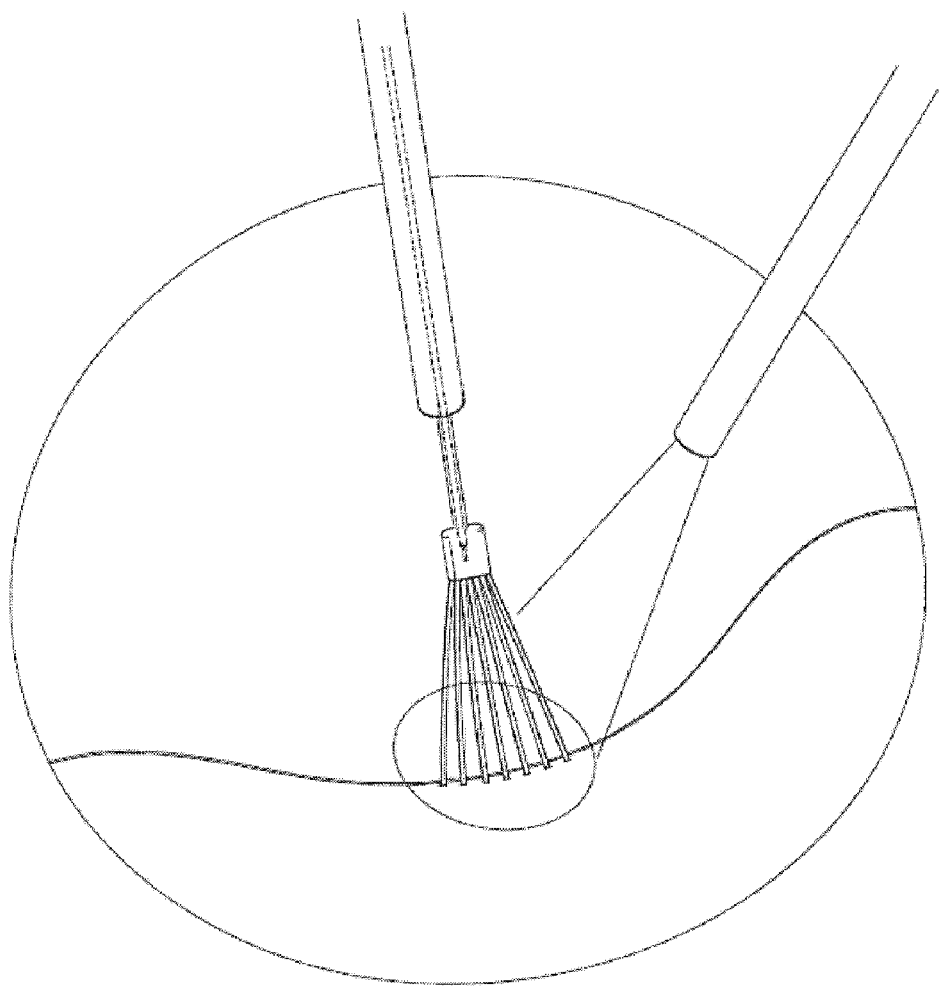
FIG. 4A illustrates medical devices, including a retinal rake, which can be modified according to the subject invention.
Figure 4B:
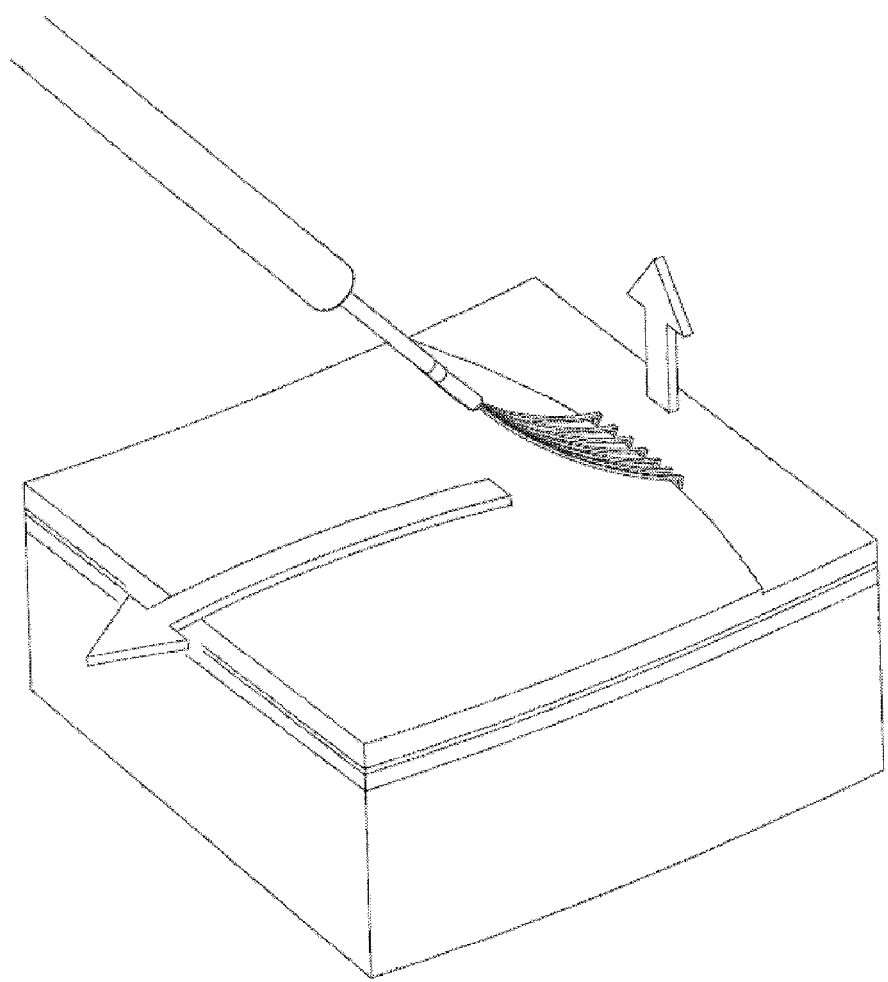
FIG. 4B illustrates the medical devices of FIG. 4A being used to treat or remove in vivo epiretinal membranes.
Figure 4C:
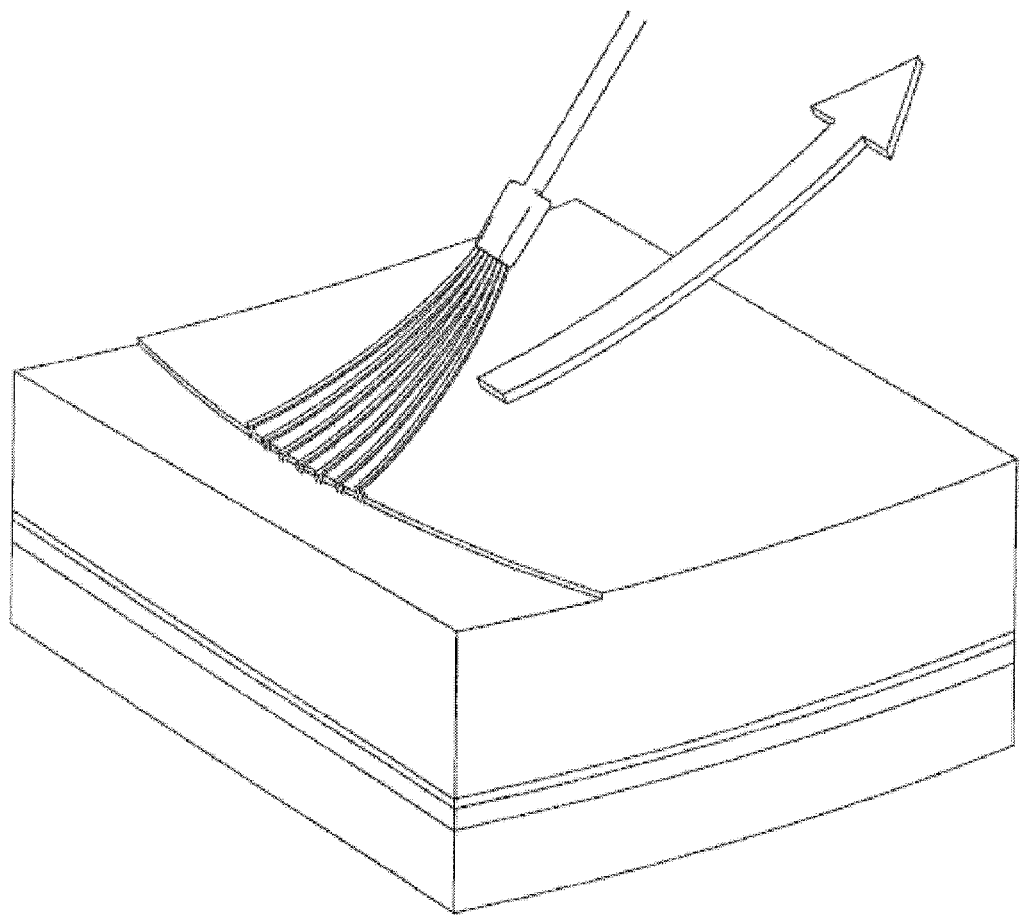
FIG. 4C illustrates the action caused by typical medical devices to treat or remove epiretinal membranes.

It can be seen in FIG. 3B that a typical retinal rake, like the Glaser Flexible Rake, usually removes sections of tissue, such as ERMs, by layers often only a few cells in thickness. In this way, the surface of a retina can be cleared of ERM to provide better light access to the retina which in many cases can improve vision.

The instruments of the subject invention are particularly useful for surgeries where tissue to be removed or destroyed is in close proximity to desired tissue. In particularly preferred embodiments, the instruments can be used to remove or destroy unwanted tissue that is adjacent to particularly sensitive tissue. Thus, in addition to the retinal surgery exemplified herein, the instruments and methods of the subject invention can be used to remove tissue that is adjacent to nerves. In specific embodiments, the devices and methods of the subject invention can be used to remove tumors and/or herniated disks that are adjacent to nerves, including the spinal cord and associated nerve roots. The devices and methods can also be used for delicate brain surgery. In addition to removal of the tissue from the location by, for example, cutting or scraping, the removal can also be achieved by destruction through physical or chemical means. The physical means can be through, for example, heat or laser treatment.

Reference herein to "treatment" includes, for example, delivering materials such as medicaments to a desired location. The medicaments may be, for example, therapeutic compounds (including small organic or inorganic compounds, gene therapies, and sustained release formulations) and chemo- or radio-therapeutic compounds that can be used to, for example, kill cancer cells. Diagnostic imaging solutions can also be delivered using the devices and methods of the subject invention. In one embodiment, the medicament can be delivered using a hypodermic needle, or other such device, that is designed as described herein such that the person using the device can accurately assess which tissue the device has entered.

In one embodiment of the subject invention, a retinal rake is augmented to include a signal detector to indicate the type of tissue being removed, touched or otherwise manipulated by the rake. To accomplish this, the rake 10 is modified to include at least two electrodes. The two electrodes can function as a bipolar pair. In a preferred embodiment, the at least two electrodes are electrically isolated. In one embodiment, a first electrode 20 can be positioned such that, during a procedure, at least a portion of the first electrode 20 can be in continual contact with the vitreous humor of an eye. In one embodiment, the first electrode 20 is introduced into the vitreous humor as a component separate from the rake 10 or other similar device. However, in a more preferred embodiment, the first electrode 20 can be affixed to, but electrically isolated from, the rake shank 25. In a still more preferred embodiment, the first electrode 20 and the second electrode 35 are affixed such that the portion of the second electrode 35 in contact with the vitreous humor is positioned relatively close to the rake end 30, for example as shown in FIGS. 1 and 3B. This permits the first electrode 20 to be presented simultaneously with the rake end 30 into an eye.

The second electrode 35 can be positioned at or near the rake end 30, and is electrically isolated from the first electrode 20. In a further embodiment, the second electrode 35 is also electrically isolated from the rake 10 and/or the rake end 30. However, in a still further embodiment, the electrically isolated second electrode 35 is positioned so that the electrically active (non-electrically isolated) end of the second electrode 35 is generally parallel or even with the section of the rake tines 38 that is used to contact tissue(s). This allows the second electrode 35 to simultaneously contact the same tissue as the rake tines 38. Alternatively, the electrically active end of the second electrode 35 can be longer or shorter than the rake tines 38, or contacting end of a similar device.

In yet a further embodiment, the second electrode 35 can be split to comprise two or more electrically active contact ends such that two or more areas of the rake tines 38 can be monitored. By way of example, each end of a row of rake tines 38 can have a contact for the second electrode 35. In a still further embodiment, additional contacts can be positioned at or near other sections of the rake tines 38, for further monitoring and feedback of tissue contact. In this embodiment, those areas of the rake tines 38 with a second electrode 35 contact can be monitored with regard to the type of tissue the retinal rake 10 contacts.

Very often optical surgical instruments, including retinal rakes known in the art, comprise metallic materials, which are capable of withstanding sterilization procedures, but still maintain proper shape and tensile strength. Thus, optical surgical instruments often comprise, for example, but are not limited to, titanium, stainless steel, sterling silver, aluminum, or combinations thereof. Advantageously, most of the metallic materials utilized are able to convey, at least to some degree, an electrical signal.

Therefore, in a preferred embodiment of the subject invention, a retinal rake, or similar device, comprises one or more materials able to conduct an electrical signal. In a further preferred embodiment, the retinal rake 10, or similar device, of appropriately conductive material is augmented to act as the second electrode 35 in the bipolar pair. In a yet further preferred embodiment, the retinal rake is almost entirely insulated such that only a portion of the rake end 30, at or near the rake tines 38, remains exposed. In this embodiment, the retinal rake is protected from random electrical signals from surrounding tissue, structure or fluids and is thus able to detect more exact electrical signals from the tissues, structures, etc. under direct manipulation or contact during a surgical procedure.

In use, the first electrode 20 and the second electrode 35 are utilized to detect a change in electrical impedance created by, and indicative of, contact with different types tissues, fluids, or structures. The electrodes are operably connected to various input amplification and output electronic components capable of interpreting the detected impedance, or lack thereof, and determining from the impedance signal the type of tissue, fluid, or structure contacted, and producing one or more appropriate visual, audio or tactile signals. Thus, the type of signal generated by the device of the subject invention can identify what type of tissue, fluid, or structure has been contacted with the one or more second electrodes.

In one embodiment, the retinal rake 10 of the subject invention provides a visual signal, such as, for example, one or more lights that may further be of one or more colors or shapes. The type of light turned on or off can indicate the tissue type in contact with the second electrode 35. In an alternative embodiment, the retinal rake 10 of the subject invention provides a tactile signal, such as vibration, heat, cold, pressure, etc. In this embodiment, the type of tactile signal can indicate the tissue type in contact with the second electrode 35.

In a preferred embodiment, the components of the retinal rake 10 generate one or more selectable audio signals, e.g., tones, beeps, whistles, etc. to identify the type of contacted tissue. In a particularly preferred embodiment, the device generates a certain tone when the electrodes are not in contact with any tissues, such as when held in the vitreous humor, a different tone when the second electrode contacts electrically inactive tissue or structure, such ERM, and another tone when the second electrode contacts electrically active tissue, such as the retina. Further embodiments, can include additional tones or sounds to indicate contact with other structures, such as choroid tissue, schlera, etc.

In an alternative embodiment, the components within the device can also determine different levels of signal intensity to indicate proximity to a tissue. For example, a second electrode that is in close proximity to a particular tissue, but not in direct contact with the tissue may emit the particular tone or sound selected for that particular tissue, but at a lower or higher volume, or at increasing or decreasing intermittent beeps, etc. to indicate a device's proximity to the tissue. This permits devices to be used as more accurate probes or indicators while being used during a surgical procedure.

The signal device used with the subject invention can be positioned in any of a variety of locations within appropriate visual, audio, or tactile contact with a physician. For example, the signals can be generated by electrical components in operable contact with the electrodes, but placed elsewhere in the room (e.g., on a desktop), one or more other rooms, or one or more remote locations.

In a preferred embodiment, the retinal rake is modified to include "on-board" components capable of detecting the various impedance levels, determining the appropriate one or more signals for the measured impedance levels, and emitting a signal indicative of that impedance level. In a further preferred embodiment, one or more auditory signals are generated that correspond to the impedance caused by a tissue, fluid or structure in contact with the second electrode. In a still further preferred embodiment, the retinal rake and the "on-board" components are self-contained so as to be hand held.

In a yet further preferred embodiment, the on-board components are contained within a handle 28. In an alternative embodiment, the self-contained, hand-held retinal rake 10 further comprises connecting components or devices that allow it to be connected to separate devices, viewing apparatus, power sources, etc. if necessary or desired.

The components necessary to carry out the subject invention and apply the novel principles discussed herein can be accomplished by any of a variety of different equipment and devices and can include various modifications, both as to equipment details and operating procedures without departing from the scope of the invention itself. While the invention is described with reference to specific details of certain circuit embodiments thereof, it is not intended that such details be regarded as limiting, except to the extent that such details are included in the accompanying claims.

Figure 2:
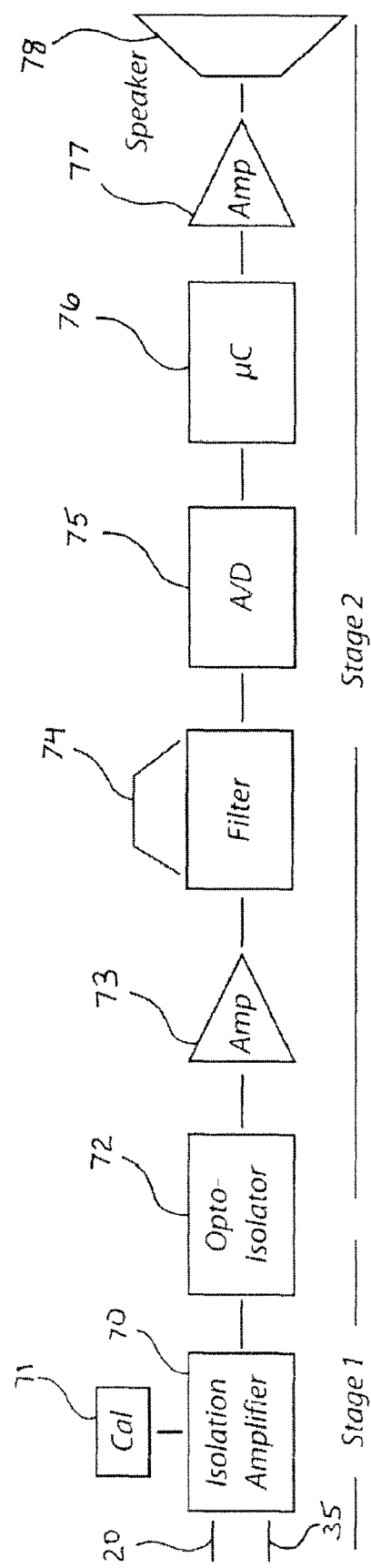
FIG. 2 is a block diagram illustrating the input, amplification and output electronics of an embodiment of the device of the subject invention.

One embodiment of a circuit 60 that can be used in accordance with the augmented retinal rake 10 of the subject invention is shown in, for example, the block diagram of FIG. 2. It can be seen in this block diagram example that the processing of the impedance signal from the electrodes comprises generally two stages. At stage 1, the circuit comprises at least one first electrode 20 and at least one second electrode 35 operably connected to the circuit 60 through an isolation amplifier 70. The isolation amplifier 70 isolates the analog impedance signals from the electrodes, 20 and 35, and sufficiently amplifies those signals so that they can be more precisely isolated by other components in the system. In order to accurately detect a change in impedance, the circuitry would be preferably calibrated against the inherent conductivity of an individual's vitreous humor. Therefore, in a further embodiment, the circuit 60 includes an appropriate calibration circuit 71. An optoisolator 72 can be coupled to the isolation amplifier 7 to isolate the electrode impedance signal from the random electrical signals, usually generated by the power source for the retinal rake 10.

The device of the subject invention can be configured to utilize A/C or D/C current. As mentioned above, the device is preferably hand-held with the components of the circuit 60 contained within a handle 28. Therefore, in a preferred embodiment, the device is operated on D/C (battery) power, which is also capable of being contained within the handle 28.

At stage 2 the signal from the optoisolator 72 can be passed through an amplifier 73 and filter 74 to further isolate the analog impedance signal. The further isolated signal can be converted by an analog/digital (A/D) converter 75 with the subsequent digital signal being processed by a microchip, microcontroller, or Field Programmable Gate Array (FPGA) chip 76 programmed to analyze the converted digital signal, determine the appropriate sound or tone for the level of the input signal received, the input signal being tissue specific, and transmit an output signal to a digital amplifier 77 and speaker 78 to generate an audible tone or sound selected to be indicative of the particular tissue, fluid, or structure. The physician upon hearing the tone or sound can adjust the position of the rake tines 38 to avoid contact with retinal tissue.

In alternative embodiments, various components of the retinal rake circuit described above can be incorporated into a single chip, or one or more microchips or FPGAs 76. For example, the isolation amplifier can be made from a single-package instrumentation amplifier, known in the art. Further, utilizing known FPGA technology, a microcontroller with onboard A/D and filtering can be used for calibration, filtering and speaker tone generation. A person with skill in the art and benefit of the subject disclosure will be able to determine various other modifications to these embodiments and such modification are contemplated to be within the scope of the subject invention.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A retinal rake comprising:
   an at least one first electrode;
   an at least one second electrode for contacting tissue;
   a circuit operably connected to the first and second electrode and configured to receive one or more impedance signals generated between the first and second electrode when said second electrode contacts a tissue, identify a level of impedance signal, and emit an observable signal indicative of the level of impedance signal,
   wherein the retinal rake comprises a shank to which is attached, at one end, a plurality of tines, and wherein the at least one first electrode is affixed to the shank and the at least one second electrode is located at or near the tines.

2. The retinal rake, according to claim 1, wherein the second electrode comprises at least a portion of the tines of the retinal rake.

3. A method for treating or removing tissue from the eye wherein said method utilizes a retinal rake comprising:
   an at least one first electrode;
   an at least one second electrode for contacting tissue;
   a circuit operably connected to the first and second electrode and configured to receive one or more impedance signals generated between the first and second electrode when said second electrode contacts a tissue, identify the level of impedance signal, and emit one or more observable signals indicative of one or more levels of impedance signal,
   wherein the retinal rake comprises a shank to which is attached, at one end, a plurality of tines, and wherein the at least one first electrode is affixed to the shank and the at least one second electrode is located at or near the tines, and
   wherein said method comprises inserting the retinal rake into a site in the eye where tissue is to be removed or treated, using the retinal rake to treat or remove tissue while simultaneously observing the signals emitted by the retinal rake and adjusting a position of the retinal rake in response to the emitted signals.

4. The method, according to claim 3, wherein said method is used to remove tissue.

5. The method, according to claim 4, wherein the retinal rake removes epiretinal tissue.

6. The method, according to claim 3, wherein the retinal rake delivers a medicament.

7. The method, according to claim 6, wherein the medicament is used to destroy unwanted tissue.

8. The method, according to claim 3, wherein the second electrode comprises at least a portion of the tines of the retinal rake.

* * * * *